United States Patent [19]

Staples et al.

[11] Patent Number: 5,169,936
[45] Date of Patent: Dec. 8, 1992

[54] PROTEIN PURIFICATION ON IMMOBILIZED METAL AFFINITY RESINS EFFECTED BY ELUTION USING A WEAK LIGAND

[75] Inventors: Mark A. Staples; Christopher A. Pargellis, both of Boston, Mass.

[73] Assignee: Biogen, Inc., Cambridge, Mass.

[21] Appl. No.: 338,991

[22] Filed: Apr. 14, 1989

[51] Int. Cl.$^5$ .................. C07K 15/06; C07K 3/18; C07K 3/28
[52] U.S. Cl. .................. 530/350; 530/413; 530/414; 530/415; 530/416; 530/417; 530/418; 530/420; 530/427; 530/395; 530/419
[58] Field of Search .............. 530/350, 395, 413, 414, 530/415, 416, 417, 418, 420, 427, 419

[56] References Cited

U.S. PATENT DOCUMENTS

| | | | |
|---|---|---|---|
| 4,423,158 | 12/1983 | Porath | 521/32 |
| 4,472,509 | 9/1984 | Gansow et al. | 436/548 |
| 4,551,271 | 11/1985 | Hochuli | 260/112 |
| 4,569,794 | 2/1986 | Smith et al. | 260/113 |
| 4,777,242 | 10/1988 | Nelles | 530/351 |

FOREIGN PATENT DOCUMENTS

| | | |
|---|---|---|
| 0118808 | 2/1984 | European Pat. Off. |
| 0253303 | 7/1987 | European Pat. Off. |
| 2782/86 | 7/1986 | Switzerland |

OTHER PUBLICATIONS

Christie et al., "Amino Acid Sequences of the Bb from Complement Factor B", Biochem. J., 209, pp. 61-70 (1983).

Fanou-Ayi and Vijaylakshmi, "Metal-Chelate Affinity Chromatography as a Separation Tool", Annals New York Academy of Sciences, 413, pp. 300-306 (1983).

Fatiadi et al., "Affinity Chromatrography and Metal Chelate Affinity Chromatography", CRC Reviews in Analytical Chemistry, 18, pp. 1-44. (1987).

Figueroa et al., "High-Performance Immobilized-Metal Affinity Chromatography of Proteins on Iminodiacetic Acid Silica-Based Bonded Phases", J. Chromatography, 371, Academia Sinica, pp. 335-352 (1986).

Hansson and Kagedal, "Adsorption and Desorption of Proteins in Metal Chelate Affinity Chromatography", J. Chromatography, 215, pp. 333-339 (1981).

Hochuli et al. "New Metal Chelate Adsorbent Selective for Proteins and Peptides Containing Neighboring Histidine Residues", J. Chromatography, 411, pp. 177-184 (1987).

Hubert and Porath, "Metal Chelate Affinity Chromatography", J. Chromatography, 198, pp. 247-255 (1980).

Kato et al., "High Perfornace Metal Chelate Affinity Chromatography of Proteins", J. Chromatography, 354, pp. 511-517 (1986).

Kikuche and Watanabe, "Significance of Use of Amino Acids and Histamine for the Elution of Non-Histone Proteins in Copper-Chelate Chromatography", Analytical Biochem., 115, pp. 109-112 (1981).

Lebreton, "Purification of the Human Plasma Alpha$_2$-SH Glycoprotein by Zinc Chelate Affinity Chromatography", Febs Letters, 80, pp. 351-354 (1977).

(List continued on next page.)

Primary Examiner—Margaret Moskowitz
Assistant Examiner—Keith C. Furman
Attorney, Agent, or Firm—James F. Hale, Jr.

[57] ABSTRACT

A process for the purification of proteins from solutions containing contaminants of similar net charge and molecular weight is provided, comprising contacting a solution containing the desired protein with an immobilized metal affinity chromatography resin in a buffer containing a low concentration of a weak ligand for the chelant of the resin. The adsorbed protein is then eluted using a buffer having a high concentration of the same weak ligand, e.g., Tris. Particularly preferred features employ agarose-iminodiacetic acid resins having copper cations and are especially useful in obtaining preparations of homogeneous, stable rsT4 proteins.

32 Claims, 4 Drawing Sheets

OTHER PUBLICATIONS

Lonnerdal et al., "Isolation of Lactoferrin from Human Milk by Metal-Chelate Affinity Chromatography", *Febs. Letters*, 75, pp. 89-92 (1988).

Lonnerdal and Keen, "Metal Chelate Affinity Chromatography of Proteins", *J. Applied Biochem.*, 4, pp. 203-208 (1982).

Ortel et al., "Separation of Copper-Binding Peptides from Human Ceruloplasmin by Metal Chelate Affinity Chromatography and HPLC", *Proteins of the Biological Fluids*, pp. 671-676 (Pergamon Press 1982).

Porath et al., "Metal Chelate Affinity Chromatography, a New Approach to Protein Fractionation", Nature, 258, pp. 598-599 (1975).

Sulkowski, "Purification of Proteins by IMAC", *Trends in Biotechnology*, 3, pp. 1-7 (1985).

Xi, "Application of Metal Chelate Affinity Chromatography in Peptide and Protein Research", pp. 8-12 (1979) (with translation).

Zawistowski et al., "Fractionation of Jerusalem Artichoke Phenolase by Immobilized Coper Affinity Chromatography", *Phytochemistry*, 26, pp. 2905-2907 (1987).

Rijken et al. 1979, *Biochemica et. Biophysica Acta 580:140-153*.

Porath et al. 1983. *Biochemistry* 22:1621-1630.

Sofer et al, 1983. Biotechnique 1(4):298-203.

FIG. 1

Amino Acid Sequence of Transmembrane T4 (CD4) (Maddon et al.)

| | |
|---|---:|
| MetAsnArgGlyValProPheArgHisLeuLeuLeuValLeuGlnLeuAlaLeuLeuPro | 20 |
| AlaAlaThrGlnGlyAsnLysValValLeuGlyLysLysGlyAspThrValGluLeuThr | 40 |
| CysThrAlaSerGlnLysLysSerIleGlnPheHisTrpLysAsnSerAsnGlnIleLys | 60 |
| IleLeuGlyAsnGlnGlySerPheLeuThrLysGlyProSerLysLeuAsnAspArgAla | 80 |
| AspSerArgArgSerLeuTrpAspGlnGlyAsnPheProLeuIleIleLysAsnLeuLys | 100 |
| IleGluAspSerAspThrTyrIleCysGluValGluAspGlnLysGluGluValGlnLeu | 120 |
| LeuValPheGlyLeuThrAlaAsnSerAspThrHisLeuLeuGlnGlyGlnSerLeuThr | 140 |
| LeuThrLeuGluSerProProGlySerSerProSerValGlnCysArgSerProArgGly | 160 |
| LysAsnIleGlnGlyGlyLysThrLeuSerValSerGlnLeuGluLeuGlnAspSerGly | 180 |
| ThrTrpThrCysThrValLeuGlnAsnGlnLysLysValGluPheLysIleAspIleVal | 200 |
| ValLeuAlaPheGlnLysAlaSerSerIleValTyrLysLysGluGlyGluGlnValGlu | 220 |
| PheSerPheProLeuAlaPheThrValGluLysLeuThrGlySerGlyGluLeuTrpTrp | 240 |
| GlnAlaGluArgAlaSerSerSerLysSerTrpIleThrPheAspLeuLysAsnLysGlu | 260 |
| ValSerValLysArgValThrGlnAspProLysLeuGlnMetGlyLysLysLeuProLeu | 280 |
| HisLeuThrLeuProGlnAlaLeuProGlnTyrAlaGlySerGlyAsnLeuThrLeuAla | 300 |
| LeuGluAlaLysThrGlyLysLeuHisGlnGluValAsnLeuValValMetArgAlaThr | 320 |
| GlnLeuGlnLysAsnLeuThrCysGluValTrpGlyProThrSerProLysLeuMetLeu | 340 |
| SerLeuLysLeuGluAsnLysGluAlaLysValSerLysArgGluLysAlaValTrpVal | 360 |
| LeuAsnProGluAlaGlyMetTrpGlnCysLeuLeuSerAspSerGlyGlnValLeuLeu | 380 |
| GluSerAsnIleLysValLeuProThrTrpSerThrProValGlnProMetAlaLeuIle | 400 |
| ValLeuGlyGlyValAlaGlyLeuLeuLeuPheIleGlyLeuGlyIlePhePheCysVal | 420 |
| ArgCysArgHisArgArgArgGlnAlaGluArgMetSerGlnIleLysArgLeuLeuSer | 440 |
| GluLysLysThrCysGlnCysProHisArgPheGlnLysThrCysSerProIle | 458 |

FIG. 2

Amino Acid Sequence of rsT4 Protein

| | |
|---|---|
| AsnLysValValLeuGlyLysLysGlyAspThrValGluLeuThrCysThrAlaSerGln | 20 |
| LysLysSerIleGlnPheHisTrpLysAsnSerAsnGlnIleLysIleLeuGlyAsnGln | 40 |
| GlySerPheLeuThrLysGlyProSerLysLeuAsnAspArgAlaAspSerArgArgSer | 60 |
| LeuTrpAspGlnGlyAsnPheProLeuIleIleLysAsnLeuLysIleGluAspSerAsp | 80 |
| ThrTyrIleCysGluValGluAspGlnLysGluGluValGlnLeuLeuValPheGlyLeu | 100 |
| ThrAlaAsnSerAspThrHisLeuLeuGlnGlyGlnSerLeuThrLeuThrLeuGluSer | 120 |
| ProProGlySerSerProSerValGlnCysArgSerProArgGlyLysAsnIleGlnGly | 140 |
| GlyLysThrLeuSerValSerGlnLeuGluLeuGlnAspSerGlyThrTrpThrCysThr | 160 |
| ValLeuGlnAsnGlnLysLysValGluPheLysIleAspIleValValLeuAlaPheGln | 180 |
| LysAlaSerSerIleValTyrLysLysGluGlyGluGlnValGluPheSerPheProLeu | 200 |
| AlaPheThrValGluLysLeuThrGlySerGlyGluLeuTrpTrpGlnAlaGluArgAla | 220 |
| SerSerSerLysSerTrpIleThrPheAspLeuLysAsnLysGluValSerValLysArg | 240 |
| ValThrGlnAspProLysLeuGlnMetGlyLysLysLeuProLeuHisLeuThrLeuPro | 260 |
| GlnAlaLeuProGlnTyrAlaGlySerGlyAsnLeuThrLeuAlaLeuGluAlaLysThr | 280 |
| GlyLysLeuHisGlnGluValAsnLeuValValMetArgAlaThrGlnLeuGlnLysAsn | 300 |
| LeuThrCysGluValTrpGlyProThrSerProLysLeuMetLeuSerLeuLysLeuGlu | 320 |
| AsnLysGluAlaLysValSerLysArgGluLysAlaValTrpValLeuAsnProGluAla | 340 |
| GlyMetTrpGlnCysLeuLeuSerAspSerGlyGlnValLeuLeuGluSerAsnIleLys | 360 |
| ValLeuProThrTrpSerThrProValGlnProMetAlaLeuIle | 375 |

FIG. 3

Amino Acid Sequence of Fragment Bb from Human Complement Factor B

| | |
|---|---:|
| LysIleValLeuAspProSerGlySerMetAsnIleTyrLeuValLeuAspGlySerAsp | 20 |
| SerIleGlyAlaSerAsnPheThrGlyAlaLysLysCysLeuValAsnLeuThrGluLys | 40 |
| ValAlaSerTyrGlyValLysProArgTyrGlyLeuValThrTyrAlaThrTyrProLys | 60 |
| IleTrpValLysValSerGluAlaAspSerSerAsnAlaAspTrpValThrLysGlnLeu | 80 |
| AsnGluIleAsnTyrGluAspHisLysLeuLysSerGlyThrAsnThrLysLysAlaLeu | 100 |
| GlnAlaValTyrSerMetMetSerTrpProAspAspValProProGluGlyTrpAsnArg | 120 |
| ThrArgHisValIleIleLeuMetThrAspGlyLeuHisAsnMetGlyGlyAspProIle | 140 |
| ThrValIleAspGluIleArgAspLeuLeuTyrIleGlyLysAspArgLysAsnProArg | 160 |
| GluAspTyrLeuAspValTyrValPheGlyValGlyProLeuValAsnGlnValAsnIle | 180 |
| AsnAlaLeuAlaSerLysLysAspAsnGluGlnHisValPheLysValLysAspMetGlu | 200 |
| AsnLeuGluAspValPheTyrGlnMetIleAspGluSerGlnSerLeuSerLeuCysGly | 220 |
| MetValTrpGluHisArgLysGlyThrAspTyrHisLysGlnProTrpGlnAlaLysIle | 240 |
| SerValIleArgProSerLysGlyHisGluSerCysMetGlyAlaValValSerGluTyr | 260 |
| PheValLeuThrAlaAlaHisCysPheThrValAspAspLysGluHisSerIleLysVal | 280 |
| SerValGlyGlyGluLysArgAspLeuGluIleGluValValLeuPheHisProAsnTyr | 300 |
| AsnIleAsnGlyLysLysGluAlaGlyIleProGluPheTyrAspTyrAspValAlaLeu | 320 |
| IleLysLeuLysAsnLysLeuLysTyrGlyGlnThrIleArgProIleCysLeuProCys | 340 |
| ThrGluGlyThrThrArgAlaLeuArgLeuProProThrThrThrCysGlnGlnGlnLys | 360 |
| GluGluLeuLeuProAlaGlnAspIleLysAlaLeuPheValSerGluGluGluLysLys | 380 |
| LeuThrArgLysGluValTyrIleLysAsnGlyAspLysLysGlySerCysGluArgAsp | 400 |
| AlaGlnTyrAlaProGlyTyrAspLysValLysAspIleSerGluValValThrProArg | 420 |
| PheLeuCysThrGlyGlyValSerProTyrAlaAspProAsnThrCysArgGlyAspSer | 440 |
| GlyGlyProLeuIleValHisLysArgSerArgPheIleGlnValGlyValIleSerTrp | 460 |
| GlyValValAspValCysLysAsnGlnLysArgGlnLysGlnValProAlaHisAlaArg | 480 |
| AspPheHisIleAsnLeuPheGlnValLeuProTrpLeuLysGluLysLeuGlnAspGlu | 500 |
| AspLeuGlyPheLeu | 505 |

PROTEIN PURIFICATION ON IMMOBILIZED METAL AFFINITY RESINS EFFECTED BY ELUTION USING A WEAK LIGAND

TECHNICAL FIELD OF THE INVENTION

This invention relates to a process for purifying proteins. More particularly, the invention relates to a process for purifying proteins containing surface metal-binding amino acid residues such as histidine and cysteine.

BACKGROUND

Various chromatography techniques are known in the art for purifying proteins. Procedures such as molecular sieve chromatography, ion exchange chromatography, and electrophoresis are commonly utilized to purify proteins. Separation of proteins that have very similar molecular weights and similar net charges, however, requires the use of alternative purification methods due to the absence of any significant differential in the features (i.e., molecular weight and net charge) which known separation processes exploit. Complete and efficient separation of proteins intended for therapeutic use is critical, particularly if the purified protein is to be used in the treatment of hypersensitive individuals such as immunodeficient or immunocompromised patients.

An alternative technique for purifying proteins under limited conditions has been named "Immobilized Metal Affinity Chromatography" (IMAC). The development of this method resulted from the recognition that certain proteins have an affinity for heavy metal ions, which could be an additional distinguishing feature to use in attempting separation of the proteins. This feature applies especially to proteins containing histidine or cysteine residues, which have been found to complex with chelated zinc or copper ions and become adsorbed on a chelating resin [J. Porath et al., "Metal Chelate Affinity Chromatography, A New Approach To Protein Fractionation," *Nature*, 258, pp. 598-99 (1975)].

A difficulty with the technique arises, however, in selectively desorbing the proteins from the resin. A common technique for desorption is lowering the pH to about 3 or 4 [A. J. Fatiadi, "Affinity Chromatography And Metal Chelate Affinity Chromatography," *CRC Critical Reviews in Analytical Chemistry*, 18, pp. 1-44 (1987)]. Another method consists of adding solutes to the eluent which have a stronger affinity than the proteins for binding to the chelated metal. This involves using strong complexing agents such as histidine or EDTA, which bind tightly to the metal [A. Figueroa et al., "High-Performance Immobilized-Metal Affinity Chromatography Of Proteins On Iminodiacetic Acid Silica-Based Bonded Phases," *J. Chromatography*, 371, pp. 335-52 (1986)].

With the latter technique, the metal is often stripped from the column; such "bleeding" of the metal ions is obviously an unwanted effect in a purification process. Figueroa et al. reported the use of ammonia, a weak competing ligand, as an eluent to desorb slightly bound proteins from an IMAC column. Their procedure, however, involved the use of HPLC and of a complex binding buffer system, requiring additional washings of the column and switching to ammonia for elution. Both of these factors add to the time involved in running the purification and detract from the efficiency and yield of the purification process.

In addition, the commonly used technique of lowering the pH to desorb proteins from the column is generally effective only for desorption of strongly bound proteins, since low pH desorption often promotes nonselective desorption of all proteins.

Genetic engineering technology has made possible the production of recombinant proteins in quantities hitherto unavailable. However, these proteins often have major contaminants which have presented an obstacle in purifying the proteins into pharmaceutically acceptable form. Current purification procedures are only partially effective in the purification of proteins found with contaminant proteins having similar molecular weight and net charge. As a result there is a continuing need for methods for purifying such proteins so as to increase the availability of new therapeutic agents.

SUMMARY OF THE INVENTION

This invention solves the problems referred to above by providing a process for the purification, in high yield, of proteins containing surface metal-binding amino acid residues. In a particularly preferred embodiment, the process of this invention allows the purification of soluble T4 protein by selective desorption from a $Cu^{2+}$-IDA substrate using the same buffer for binding and for eluting the proteins from the substrate.

The present invention provides a method for separating proteins based on the nature and distribution of their constituent amino acids.

More particularly, the present invention provides a method for separating proteins according to the affinity of their constituent amino acid residues for specific metal cations.

The present invention further provides a method for separating proteins from contaminants of substantially similar molecular weight and net charge.

Thus, the present invention encompasses a process for purifying a protein having surface metal-binding amino acid residues by the steps:

(a) preparing an immobilized metal affinity chromatography (IMAC) resin comprising a matrix resin linked to a bidentate chelator having bound divalent metal ions ($Me^{2+}$), in a binding buffer containing a weak ligand for said metal ions, such as Tris, ammonia, and the like, (b) contacting a solution containing the protein (which may also contain contaminant protein(s) or protein fragments of similar net charge and molecular weight) with the resin, and (c) selectively eluting the protein using a buffer containing a higher concentration of the weak ligand than in the equilibration buffer.

As alluded to above, the present invention may be advantageously applied in the purification of a protein gaining particular interest in the investigation of acquired immune deficiency syndrome (AIDS), namely, soluble T4 (CD4).

T4 proteins serve as the receptors on the surface of T4+ lymphocytes. In immunocompetent individuals, T4+ lymphocytes interact with other specialized cell types of the immune system to confer immunity to or defense against infection [E. L. Reinherz and S. F. Schlossman, "The Differentiation and Function of Human T Lymphocytes," *Cell*, 19, pp. 821-27 (1980)]. More specifically, T4 lymphocytes stimulate production of growth factors which are critical to a functional immune system. For example, they act to stimulate B cells, the descendants of hemopoietic stem cells, which promote the production of defensive antibodies. They also activate macrophages ("killer cells") to attack infected or otherwise abnormal host cells, and they induce monocytes ("scavenger cells") to encompass and destroy invading microbes.

The primary target or receptor for certain infective agents is the T4 surface protein. These agents include, for example, viruses and retroviruses. When T4 lymphocytes are exposed to such agents, they are rendered nonfunctional. As a result, the host's complex immune defense system is destroyed and the host becomes susceptible to a wide range of opportunistic infections.

Such immunosuppression is seen in patients suffering from acquired immune deficiency syndrome ("AIDS"). Complete clinical manifestation of AIDS is usually preceded by AIDS related complex ("ARC"). The human immunodeficiency virus ("HIV") is thought to be the etiological agent responsible for AIDS infection and its precursor, ARC [M. G. Sarngadharan et al., Antibodies Reactive With Human T-Lymphotropic Retroviruses (HTLV-III) In The Serum of Results With AIDS," *Science*, 224, pp. 506–08 (1984)].

The host range of HIV is associated with cells which bear the surface glycoprotein T4. The tropism of HIV for T4+ cells is attributed to the role of the T4 cell surface glycoprotein as the membrane-anchored virus receptor. Because T4 behaves as the HIV receptor, its extracellular sequence probably plays a direct role in binding HIV. A cloned cDNA version of human T4, when expressed on the surface of transfected cells from non-T cell lineages, including murine and fibroblastoid cells, endows those cells with the ability to bind HIV [P. J. Maddon et al., "The T4 Gene Encodes The AIDS Virus Receptor And Is Expressed In The Immune System And The Brain," *Cell*, 47, pp. 333–48 (1986)].

Therapeutics based upon soluble T4 protein have been proposed for the prevention and treatment of the HIV-related infections AIDS and ARC. The nucleotide sequence and a deduced amino acid sequence for a DNA that purportedly encodes the entire human T4 protein have been reported [P. J. Maddon et al., "The Isolation And Nucleotide Sequence Of A cDNA Encoding The T Cell Surface Protein T4: A New Member Of The Immunoglobulin Gene Family," *Cell*, 42, pp. 93–104 (1985)]. The amino acid sequence is depicted in FIG. 1 herein. Based upon its deduced primary structure, the T4 protein is divided into the following domains:

| Structure/Proposed Location | Amino Acid Coordinates |
| --- | --- |
| Hydrophobic/Secretory Signal | −23 to −1 |
| Homology to V-Regions/Extracellular | +1 to +94 |
| Homology to J-Regions/Extracellular | +95 to +109 |
| Glycosylated Region/Extracellular | +110 to +374 |
| Hydrophobic/Transmembrane Sequence | +375 to +395 |
| Very Hydrophilic/Intracytoplasmic | +396 to +435 |

Soluble T4 proteins have been constructed by truncating the full length T4 protein at amino acid 375, to eliminate the transmembrane and cytoplasmic domains. Such proteins have been produced by recombinant techniques [R. A. Fisher et al., "HIV Infection Is Blocked In Vitro By Recombinant Soluble CD4," *Nature*, 331, pp. 76–78 (1988)]. Soluble T4 proteins advantageously interfere with the T4/HIV interaction by blocking or competitive binding mechanisms which inhibit HIV infection of cells expressing the T4 surface protein. Soluble T4 proteins inhibit interaction between T4+ lymphocytes and antigen presenting cells and targets of T4+ lymphocyte mediated killing. By acting as soluble virus receptors, soluble T4 proteins are useful as anti-viral therapeutics to inhibit HIV binding to T4+ cells and virally induced syncytium formation.

Thus, recombinant soluble T4 protein (rsT4), due to its activity as the HIV receptor, can be effective in the treatment of AIDS, ARC, HIV infection and other immunodeficiencies caused by T4 lymphocyte depletion or abnormalities. It is therefore desirable to produce pure forms of soluble T4 in large amounts for clinical and therapeutic uses. Particularly when the protein is to be injected into the bloodstream of immunodepressed individuals, it must be free of toxic contaminants. In order to meet this demand, the need exists for a purification method which allows efficient preparation of rsT4 free of contamination by destabilizing or toxic factors.

The soluble T4 prepared by current techniques, however, is accompanied by a contaminant (fragment Bb of complement factor B) having a similar molecular weight and charge. Thus, prior methods such as molecular sieve chromatography, ion exchange chromatography, and electrophoresis are not feasible for complete purification.

A preferred protein purified according to the process of this invention is recombinant soluble T4, the receptor on the surface of T4+ lymphocytes. The purified, stable rsT4 produced according to this invention is useful in treating immunodeficient patients suffering from diseases caused by infective agents whose primary targets are T4+ lymphocytes. More particularly, the soluble T4 protein purified according to the process of this invention is useful in preventing, treating or detecting acquired immune deficiency syndrome, AIDS related complex (ARC), and HIV infection.

A particular object of this invention is to provide purified, homogeneous, recombinant soluble T4 protein in stable conformation, which may, in turn, be used in the treatment or prevention of AIDS, ARC, and HIV infection.

In a preferred embodiment, therefore, the invention comprises the steps of (a) contacting a solution containing rsT4 protein, preferably free of source cells and cellular debris, with an immobilized metal affinity chromatography (IMAC) resin comprising a matrix resin linked to a bidentate chelator bound to divalent metal ions, in a binding buffer containing salt, such as NaCl or KCl (preferably NaCl), and a weak ligand for said metal ions, and (b) selectively eluting the rsT4 protein using a buffer containing salt and a higher concentration of the weak ligand than in the binding buffer. Preferably, the concentration of salt in the elution buffer will be about the same as that of the binding buffer, and preferably the concentration of the weak ligand in the elution buffer will be 10–50 times that of the binding buffer. Preferred matrix resins are agarose gels.

It is also preferred that solution components which may be purified by conventional means will be eliminated from the sample prior to the application of IMAC resin according to this invention. Therefore, in another preferred embodiment, the process of this invention comprises the steps: (1) contacting the culture medium containing the rsT4 protein, filtered free of the source cells which produced the rsT4, with a cationic exchange resin, which adsorbs the protein; (2) eluting the adsorbed proteins from the resin on the basis of their net charge; (3) applying the fraction or fractions of eluate from the cationic exchange resin (which will contain the rsT4 protein) to an anionic exchange resin which adsorbs contaminants while allowing rsT4 and other proteins with similar pl values to wash through without binding to the resin; (4) applying the "wash" fraction or fractions containing rsT4 to an immobilized metal affinity chromatography (IMAC) resin, prepared, e.g., by suspending a gel comprised of agarose and a bidentate chelator, e.g., iminodiacetic acid, in a solution of a metal salt, using a binding buffer containing salt (e.g., NaCl or KCl) and a low concentration (e.g., 0.010 to 0.050M) of a weak ligand for the metal ion of the metal affinity chromatography resin, and (5) eluting the rsT4 using as an eluant a buffer having the same salt concentration but a higher concentration (e.g., 0.100 to 0.500M) of the same weak ligand.

In the foregoing scheme, preferably the metal salt used in preparing the metal affinity resin will be $CuCl_2.2H_2O$; preferably the binding buffer will contain Tris.HCl as the weak ligand in a concentration of about 0.01 to 0.1M, most preferably about 0.020M; preferably the salt of the binding and elution buffers will be NaCl or KCl in a concentration (in both buffers) of about 0.10 to 1.0M; and preferably the elution buffer will contain Tris.HCl in a concentration of about 0.1 to 0.3M, most preferably about 0.2M. A gradient of Tris buffer may also be used in elution. Furthermore, as used herein, the term "weak ligand" is defined with reference to the protein to be purified (e.g., rsT4) and the particular metal affinity resin employed. The weak ligand will have a lesser affinity for the binding resin than the protein to be separated.

The resulting purified rsT4 obtained as above can be used therapeutically to prevent, treat, or detect acquired immune deficiency syndrome (AIDS), AIDS related complex (ARC), and HIV infection.

This method of preparation and purification is also useful for purifying other proteins having sufficient surface metal binding amino acid residues to bind to an IMAC column, and which are desorbed from the column with a weak competing ligand, such as Tris.HCl.

BRIEF DESCRIPTION OF DRAWINGS

FIG. 1 depicts the amino acid sequence of natural T4 (CD4) protein (a transmembrane protein), as reported by Maddon et al., *Cell*, 42, pp. 93-104 (1985).

FIG. 2 depicts the amino acid sequence of a rsT4 protein which may be advantageously purified according to the process described herein.

FIG. 3 is the amino acid sequence of fragment Bb from complement Factor B.

Figure 4:
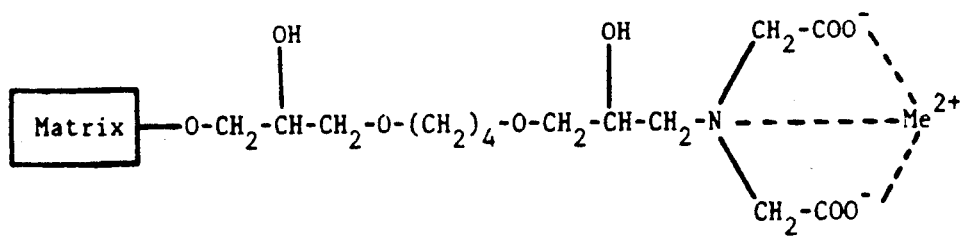
FIG. 4 is a schematic representation of an immobilized metal affinity resin useful in the process of the invention.

The process according to the invention will now be described in further detail, using the purification of a recombinant soluble T4 protein as a specific example. While the following description relates to a particular protein advantageously purified according to the invention, it will be understood that the process as described will be applicable to the separation of a wide variety of other proteins having surface metal-binding amino acids, which proteins will be immediately recognized by those skilled in this art. The following description is not intended to limit the scope of the invention in any way.

DETAILED DESCRIPTION OF INVENTION

The present invention provides a process for the purification of recombinant soluble T4 and other proteins bearing surface metal-binding amino acid residues. The process of the invention provides the protein in a stable, native conformation suitable for administration to humans.

The following discussion refers to the separation of a rsT4 protein, however the principles disclosed will be readily applicable to the purification of other proteins containing metal-binding amino acid residues, for separation from other proteins or protein fragments of similar molecular weight and charge.

A crude sample containing the rsT4 protein is obtained, for example, by suspending and incubating cells containing the gene coding for rsT4 in a cell growth medium containing collagen beads, then filtering the medium to remove the source cells. The process of the invention may include the initial step of contacting the sample containing the rsT4 with a cationic exchange resin. It is preferred that an anionic gel with a capacity of about 20 meq/ml gel or greater and a fast flow rate suitable for large-scale purification be used. Most preferably, the gel used is an anionic cross-linked agarose gel, available commercially, e.g., as "S-SEPHAROSE FAST FLOW", (Pharmacia LKB), which uses a bound anionic sulfate ligand and a maximal linear flow rate of 400 cm/h. By adjusting the initial pH to about 5.5, many proteins in the sample, including the rsT4 protein, are positively charged and will become adsorbed on the resin. The flow-through contains non-adsorbing contaminants which may be discarded. The resin can then be washed with a buffer at an increased pH and with an increased salt concentration. Any buffer with a pKa in the pH range of about 2-10 may be used. Preferably, the elution buffer is Tris.HCl at pH 8.5 and containing 0.05 to 1.0M, preferably 0.1M, concentration of a salt, preferably NaCl. Rinsing the resin with this buffer causes desorption and elution of most of the proteins contained in the original crude sample.

After washing the cationic exchange resin with the buffer solution, the fraction or fractions of eluate containing rsT4 protein may be contacted with an anionic exchange resin. Preferably such resin will have a capacity of 20 meq/ml gel or greater and a flow rate suitable for large-scale purification. Most preferably, the gel used is a cationic cross-linked agarose gel, available commercially, e.g., as "Q-SEPHAROSE FAST FLOW" (Pharmacia LKB), which uses the cation of the diethyl(2-hydroxy-propyl) amino-ethyl group and a maximal linear flow rate of 400 cm/h. Since the pH of the eluate from the cationic exchange step is about 8.5, all proteins except those with a pI in the basic range (i.e., pH above 8.5) will be negatively charged and will be adsorbed onto the resin. The flow-through will contain those proteins with a pI above 8.5, including the rsT4. This step results in approximately a 70% yield of 90% pure rsT4.

This step is particularly suited for proteins such as rsT4 which contain a large number of basic amino acid residues such as lysine, arginine and histidine. The rsT4 sequence depicted in FIG. 2, for example, contains 38 lysine residues, which makes the overall pI of the molecule unusually basic. For this reason, the use of a high pH in the anion exchange step successfully separates the rsT4 and similar proteins from the large number of protein contaminants which have a lower lysine content and consequently have pI's much closer to the norm of about 7.5. After obtaining the flow-through from the anion exchange step, major contaminants remaining are proteins (or protein fragments) also having a high number of basic residues and consequently basic pI's. In the case of rsT4, a major contaminant that remains in the solution is fragment Bb of complement factor B (see FIG. 3).

For the next step in the purification, the eluate from the anion exchange step is adjusted from pH 8.5 to pH about 7.5 with the addition of acid. Although any acid may be used to lower the pH, the acid used in this technique is preferably HCl. The salt (NaCl) concentration is also increased, preferably to 0.15M. The preparation is then directly contacted with a metal chelating resin containing bound metal cations. Any resin which can be linked with a chelating agent may be used to form the matrix for the metal cations. The preferred "matrix resin" is an agarose-based resin which is linked to iminodiacetic acid (IDA), a dicarboxylic acid group which serves as a bidentate chelator. A commercially available example is "CHELATING SEPHAROSE 6B (Pharmacia Fine Chemicals, Piscataway, N.J.)". Other resins which are inert to the solutions they are contacted with and which are capable of acting as a substrate for bidentate chelator molecules, such as iminodiacetic acid, are also suitable. Examples include dextran, cross-linked acrylamide, beaded cellulose, and the like. The resin is contacted with a divalent metal ion in order to cause chelation, or immobilization of the ion, as shown schematically in FIG. 4.

The divalent metal ion ($Me^{2+}$ in FIG. 4) is chosen from, but not limited to, the group containing Nickel-(II), Zinc(II), Cobalt(II), and Copper(II). The preferred metal for the agarose-IDA resin of this embodiment is $Cu^{2+}$ due to its stronger binding constants with IDA and with rsT4. When the flow-through from the anion exchange step is contacted with this IMAC resin, the exposed histidine residues on the proteins will bind to the immobilized metal. The rsT4 and the fragment Bb both contain histidine residues and will thus bind to the resin. The rsT4 protein, however, contains only 4 histidine residues, whereas its major contaminant, fragment Bb of complement factor B, has 13 histidine residues (cf. FIG. 2; FIG. 3).

In order to selectively elute the rsT4 from the resin, a buffer must be chosen which will compete with the proteins for binding to the metal on the basis of the strength of the protein's affinity for the copper. Buffers with a stronger affinity for the metal than the protein's affinity for the metal would not be effective in selective desorption as they would disrupt all $His-Cu^{2+}$ binding and desorb all bound proteins simultaneously. Weaker ligands such as Tris (tris(hydroxymethyl)methylammonium+) would not be expected to cause desorption since the affinity of the histidine residues on the protein for the metal is much stronger than the Tris molecule's affinity, probably due in part to the much more effective electron donation of the imidazole ring of histidine relative to the lone pair of electrons of the Tris nitrogen, and to the multiple-point attachment of the protein to the resin.

Surprisingly, however, continuing the use of Tris.HCl at an increased concentration, e.g., of 0.2M, causes sufficient saturation and competition with the rsT4's $His-Cu^{2+}$ binding to allow desorption of the rsT4 from the resin. The contaminant, however, remains adsorbed on the resin. Other weak ligands such as ammonia will also be effective in this step to accomplish desorption. Use of a different weak ligand as the eluent, however, decreases the efficiency of the process due to the need to change buffer systems to ammonia for elution.

This purification step removes the final major contaminant from the rsT4 and results in a greater than 60% yield of rsT4 which is of greater than 94% purity.

The rsT4-containing eluate from the immobilized $Cu^{2+}$ resin may be concentrated by precipitation with ammonium sulfate; and as a further preferred step of this purification, the rsT4-containing precipitate is dissolved, preferably in phosphate buffered saline (PBS), and the solution applied to a size exclusion resin which separates molecules in the range of (in this instance, for rsT4) 40,000 m.w. Preferred such size exclusion resins are cross-linked allyl dextran/N,N'-methylene bisacrylamide copolymer resins, commercially available, e.g., as "SEPHACRYL S-100 HR". Other solutions or materials may alternatively be employed for redissolving the precipitate or as the elution buffer in the size exclusion chromatography; and such alternative solutions or materials will normally be selected with an eye to the desired final formulation and whether the protein is being prepared, e.g., for storage or immediate administration to patients or some other end use. One such alternative material is glycine (e.g., about 0.5% w/v).

The pure, stable rsT4 preparation obtained as above can be diluted to the appropriate dosage strength and used directly in the treatment of immunodeficient and immunocompromised patients.

The method of this invention may be utilized for purifying any protein which contains enough metal-binding residues such as histidine or cysteine to allow binding to an immobilized metal ion chelating resin. Such proteins may be selectively desorbed from the resin using a weak competing ligand, such as Tris, for separation from similarly charged and sized contaminant proteins or protein fragments which have a differential composition or distribution of surface histidine and cysteine residues, as compared with the protein to be separated.

The following example of the purification of rsT4 protein is set forth by way of illustration of the process according to the invention.

EXAMPLE

Partial Purification of Recombinant Soluble T4 Via Cation-Exchange Chromatography We first obtained a 400L sample containing rsT4 protein by suspending and incubating cells containing the gene coding for rsT4 (CHO Clone 6, provided by Biogen, Inc., Cambridge, Mass.) on collagen beads in a bioreactor. The rsT4 is secreted as a soluble protein into the extracellular medium. We then removed the medium from the bioreactor and subjected it to 0.2 micron ultrafiltration to remove the source cells. Next, we diluted this sample with an equal volume of water and adjusted the pH to 5.5 by adding 1% acetic acid. We then loaded this solution onto a 4.0L column with a height of 6.5 cm which contained S-Sepharose, a cation exchange resin in a ratio of 140 mg protein/ml gel. We washed with 7.5 column volumes of 0.015 Tris.HCl buffer at pH 8.5. We then washed the column with 1.7 column volumes of 0.015M Tris.HCl buffer at pH 8.5, containing 0.1M NaCl, to elute the adsorbed proteins. This step produced rsT4 of about 60% purity.

Further Purification of Recombinant Soluble T4 Via Anion-Exchange Chromatography at High pH We then loaded the fractions of eluate from the cation exchange column containing rsT4, diluted with 1.1 volumes of Tris.HCl and adjusted to pH 8.5, directly onto a 2.5L column containing Q-SEPHAROSE FAST FLOW (Pharmacia), an anion exchange resin, in a ratio of 10 mg protein/ml gel. We collected the flow-through from the column and then regenerated the resin for further use. The flow-through gave about a 70% yield of 90% pure rsT4.

Preparation of Immobilized Metal Ion Column

First, we washed one column volume of CHELATING SEPHAROSE 6B TM gel with several column volumes of water. We then suspended the washed gel in four volumes of 0.05M $CuCl_2.2H_2O$ for at least 30 minutes. We then washed the gel again with several volumes of water to remove uncomplexed $Cu^{2+}$. Finally, we equilibrated the gel by washing it with several volumes of 0.02M Tris.HCl buffer (pH 7.5), containing 0.15M NaCl.

Further Purification of rsT4 by Immobilized Metal Affinity Chromatography

After pooling the flow-through from the anion exchange chromatography step, we adjusted the pH of the sample to 7.5 by addition of HCl (1.0M) and increased the salt concentration to 0.15M by addition of NaCl. We then applied the flow-through pool to a 2.5L column containing the immobilized copper resin. The sample was loaded onto the column in a ratio of 10 mg protein/ml gel and at a temperature of 4° C. The flow rate for the column was 6 column volumes/hour.

The loaded column was then washed with several column volumes of 0.02M Tris.HCl buffer (pH 7.5) containing 0.15M NaCl to allow binding of proteins and flow-through of non-binding contaminants. The column effluent was fed through a UV spectrophotometer, and the rsT4 was eluted from the column by washing with 0.2M Tris.HCl (pH 7.5) containing 0.15M NaCl, until the absorbance at 280 nm dropped to baseline. The rsT4's contaminant factor Bb remained adsorbed on the column due to its larger number of histidine residues and consequent stronger binding affinity to the immobilized copper.

This procedure resulted in a stable rsT4 preparation of approximately 95% purity.

Final Purification of rsT4 by Size Exclusion Chromatography

We added ammonium sulfate (472 g/L) to the rsT4-containing pool from the IMAC column. We collected the resulting precipitate containing the rsT4 by centrifugation (10,000 rpm at 4° C. for 1 hour) and resolubilized the precipitate in 0.5% (w/v) glycine, pH 7.0, at 10 mg/ml. The resulting solution was applied to a 25L SEPHACRYL S-100 HR gel column, at 4° C. at a flow rate for the column of 83 ml/min. We collected and pooled the central rsT4 peak, detected by absorbance at 280 nm, to obtain a protein of 98% purity. The elution buffer from the previous separation step was also exchanged in this final step for the buffer used in formulation.

We sterilized the pooled fraction by filtration on a DIAFLO YM100 TM ultrafiltration membrane (Amicon, Danvers, Mass.), then concentrated the filtrate to 5 mg/ml by ultrafiltration on a DIAFLO PM10 filter (Amicon). We adjusted this preparation to 5% (w/v) mannitol to yield an injectable composition, which was then freeze-dried in vials.

In the foregoing concentration and size exclusion step, we observed that the use of glycine retarded elution of the rsT4 from the column, giving it a slightly smaller apparent molecular weight. We substituted PBS for redissolving and eluting the rsT4, and this phenomenon was eliminated. For this reason, PBS is preferred for the final stage of rsT4 purification according to this embodiment, however in the purification of other proteins it is not expected that the use of glycine will have the same effect.

While the process of the invention has been described with reference to the separation of a particularly desirable protein, rsT4, the process will be suitable for many other proteins containing surface metal-binding amino acid residues such as histidine and/or cysteine. Such proteins include, e.g., other soluble T4 proteins, as well as human serum proteins (such as IgG, haptoglobin, hemopexin, Gc-globulin, Clq, C3, C4), human ceruloplasmin, *Dolichos biflorus* lectin, zinc-inhibited Tyr(P) phosphatases, phenolase, carboxypeptidase isoenzymes, human copper-zinc superoxide dismutase, nucleoside diphosphatase, leukocyte interferon, fibroblast interferon, immune interferon, lactoferrin, human plasma $alpha_2$-SH glycoprotein, $alpha_2$-macroglobulin, $alpha_1$-antitrypsin, plasminogen activator, gastrointestinal polypeptides, pepsin, human and bovine serum albumin, granule proteins from granulocytes and lysozymes, non-histone proteins, human fibrinogen, human serum transferrin, human lymphotoxin, calmodulin, protein A, avidin, myoglobins, somatomedins, human growth hormone, transforming growth factors, platelet-derived growth factor, alpha-human atrial natriuetic polypeptide, cardiodilatin, and others. In addition, although in the specific examples of this disclosure column chromatography is described, batch methods could also be used. The process will also be useful in the purification of other soluble proteins derived from membrane-bound proteins, i.e., by cloning of a gene coding for the extracellular region of the protein or by other techniques. All such purifications are within the intended scope of this invention as defined by the appended claims.

We claim:

1. A process for separating, in a partially purified protein sample, a protein having surface metal-binding amino acid residues from a proteinaceous impurity having similar molecular weight and molecular charge to said protein which remains associated with said protein after the partial purification of said protein sample, said process comprising the steps:

(a) contacting the partially purified protein sample with an immobilized metal affinity chromatography resin, said resin comprising a matrix resin linked to a bidendate chelator bound to divalent metal ions, in a binding buffer consisting essentially of salt and a weak ligand, the affinity of the weak ligand for the divalent metal ions being less than that of said protein and said impurity; and (b) selectively eluting the protein or the impurity using an elution buffer consisting essentially of salt and a higher concentration of the weak ligand than in the binding buffer.

2. The process according to claim 1 wherein said partial purification of the protein sample is by dialysis, ultrafiltration, density-gradient centrifugation, molecular sieve chromatography, electrophoresis, ion-exchange chromatography, affinity chromatography, hydrophobic interaction chromatography, ammonium sulfate precipitation, or combinations thereof.

3. A process according to claim 1, wherein the weak ligand is Tris.

4. A process according to claim 3, wherein the binding buffer contains about 0.01–0.1M Tris.HCl.

5. A process according to claim 3, wherein the elution buffer contains about 0.1–0.3M Tris.HCl.

6. A process according to claim 3, wherein the binding buffer is about 0.02M Tris.HCl and the elution buffer is about 0.2M Tris.HCl buffer.

7. A process according to claim 6, wherein the binding buffer contains about 0.15M NaCl, and the elution buffer also contains about 0.15M NaCl.

8. The process according to claim 1 wherein the protein is recombinant soluble T4 which has a primary structure defined by the amino acid sequence depicted in FIG. 2.

9. The process according to claim 1 wherein the divalent metal ion is $Cu^{2+}$.

10. The process according to claim 9 wherein the bidentate chelator is iminodiacetic acid.

11. The process according to claim 10 wherein the $Cu^{2+}$ ion is chelated by the iminodiacetic and immobilized on an agarose resin at about pH 5 or higher.

12. The process according to claim 1 wherein the immobilized metal affinity chromatography resin is washed with a buffer containing about 0.2M Tris.HCl at pH 7.5 and about 0.15M NaCl, following the step of contacting of the protein sample with the resin.

13. The process according to claim 1 wherein either the protein or the proteinaceous impurity adsorbed on the immobilized metal affinity chromatography resin is selectively eluted with a buffer containing Tris.HCl at a concentration of about 0.2M.

14. The process according to claim 13 wherein proteins with fewer metal-binding residues are eluted from the column first and are thus isolated.

15. The process according to claim 1, wherein the protein having surface metal-binding amino acid residues is selected from the group consisting of soluble T4, IgG, haptoglobin, hemopexin, Gc-globulin, Clq, C3, C4, human ceruloplasmin, *Dolichos biflorus* lectin, zinc-inhibited Tyr(P) phosphatases, phenolase, carboxypeptidase isoenzymes, human copper-zinc superoxide dismutase, nucleoside diphosphatase, leukocyte interferon, fibroblast interferon, immune interferon, lactoferrin, human plasma $alpha_2$-SH glycoprotein, $alpha_2$-macroglobulin, $alpha_1$-antitrypsin, plasminogen activator, gastroin-testinal polypeptides, pepsin, human and bovine serum albumin, granule proteins from granulocytes and lysozymes, non-histone proteins, human fibrinogen, human serum transferrin, human lymphotoxin, calmodulin, protein A, avidin, myoglobins, somatomedins, human growth hormone, transforming growth factors, platelet-derived growth factor, alpha-human atrial natriuetic polypeptide, and cardiodilatin.

16. In a process for purifying a protein having surface metal-binding amino acid residues which includes steps effecting the elimination of impurities on the basis of molecular weight and net charge, the improvement wherein impurities not removed in previous steps are removed by the steps:

(a) contacting the protein and remaining impurities with an immobilized metal affinity chromatography resin, said resin comprising a matrix resin linked to a bidendate chelator bound to divalent metal ions, in a binding buffer consisting essentially of salt and a weak ligand, the affinity of the weak ligand for the divalent metal ions being less than that of said protein and said impurities; and (b) selectively eluting the protein or the impurities using an elution buffer consisting essentially of salt and a higher concentration of the weak ligand than in the binding buffer.

17. The improvement according to claim 16, wherein said immobilized metal affinity chromatography resin comprises an agarose resin linked to iminodiacetic acid bound to $Cu^{2+}$ ions, and said weak ligand is tris(hydroxymethyl)methylammonium$^+$.

18. The improvement according to claim 17, wherein the protein is recombinant soluble T4 and the impurity is fragment Bb of complement factor B.

19. A process for purifying a recombinant soluble T4 protein, comprising the steps of: (1) contacting culture medium containing recombinant soluble T4, filtered free of the source cells which produced the recombinant soluble T4, with a cationic exchange resin; (2) eluting the adsorbed proteins from the resin on the basis of their net charge; (3) applying the fraction or fractions of eluate from the cationic exchange resin containing the recombinant soluble T4 to an anionic exchange resin; (4) applying the wash fraction or fractions from step (3) containing recombinant soluble T4 to an immobilized metal affinity chromatography resin, said immobilized metal affinity chromatography resin comprising a matrix linked to a bidentate chelator bound to divalent metal ions, using a binding buffer consisting essentially of a low concentration of a weak ligand for the metal ion of the immobilized metal affinity chromatography resin; and (5) eluting the recombinant soluble T4 using as an eluant a buffer consisting essentially of a higher concentration of the weak ligand than in binding buffer.

20. The process according to claim 19, further comprising the steps: (6) concentrating the eluate of step (5) containing recombinant soluble T4 by ammonium sulfate precipitation; and (7) solubilizing the precipitate of step (6) and applying the solution to a size exclusion chromatography resin.

21. The process according to claim 20 wherein, in the final step (7), the recombinant soluble T-4 containing precipitate is solubilized and subjected to size exclusion chromatography in a formulation buffer.

22. A process according to claim 21, wherein the weak ligand is Tris.

23. A process according to claim 22, wherein the binding buffer contains about 0.01–0.1M Tris.HCl.

24. A process according to claim 23, wherein the elution buffer contains about 0.1–0.3M Tris.HCl.

25. A process according to claim 22, wherein the binding buffer contains about 0.2M Tris.HCl.

26. A process according to claim 24, wherein the binding buffer contains about 0.15M NaCl, and the elution buffer also contains about 0.15M NaCl.

27. The process according to claim 21, wherein said recombinant soluble T4 has a primary structure defined by the amino acid sequence depicted in FIG. 2.

28. The process according to claim 21, wherein the divalent metal ion is $Cu^{2+}$.

29. The process according to claim 28, wherein the bidentate chelator is iminodiacetic acid.

30. The process according to claim 29, wherein the $Cu^{2+}$ ion is chelated by the iminodiacetic acid and immobilized on an agarose resin.

31. The process according to claim 21, wherein the immobilized metal affinity chromatography resin is washed with a buffer containing about 0.02M Tris.HCl at pH 7.5 and about 0.15M NaCl, following contacting of the sample containing the recombinant soluble T4 with the immobilized metal affinity chromatography resin.

32. The process according to claim 21, wherein the proteins adsorbed on the immobilized metal affinity chromatography resin are selectively eluted with a buffer containing Tris.HCl at a concentration of about 0.2M.

* * * * *